United States Patent [19]
Swanson

[11] Patent Number: 5,296,712
[45] Date of Patent: Mar. 22, 1994

[54] DETECTOR TIME-GATING FOR NEUTRON RADIOGRAPHIC IMAGING

[75] Inventor: Frank R. Swanson, Freeport, N.Y.

[73] Assignee: Grumman Aerospace Corporation, Bethpage, N.Y.

[21] Appl. No.: 974,509

[22] Filed: Nov. 12, 1992

[51] Int. Cl.$^5$ .................... G01T 3/00; G01N 23/05
[52] U.S. Cl. ............................... 250/390.02; 250/391
[58] Field of Search .................. 250/390.02, 390.07, 250/391, 392

[56] References Cited
U.S. PATENT DOCUMENTS 4,535,246  8/1985  Shani ............................ 250/390.02

FOREIGN PATENT DOCUMENTS 1226928  3/1971  United Kingdom ........... 250/390.02

Primary Examiner—Carolyn E. Fields
Attorney, Agent, or Firm—Pollock, Vande Sande & Priddy

[57] ABSTRACT

A source of neutrons is pulsed. A resultant flow of pulsed neutrons is detected and initiates a time delay. During the time delay, more quickly moving sources of radiation, such as fast and epithermal neutrons as well as gamma rays pass by an imaging device which is not turned on. Accordingly, these sources of noise are not detected. At the end of the time delay, the detecting imaging device is turned on; and during a resulting window interval, the pulsed thermal neutrons are detected and imaged after passage through an intermediately positioned object.

4 Claims, 2 Drawing Sheets

DETECTOR TIME-GATING FOR NEUTRON RADIOGRAPHIC IMAGING

FIELD OF THE INVENTION

The present invention relates to radiography, and more particularly to a pulsed detector for neutron radiographic imaging.

BACKGROUND OF THE INVENTION

The prior art includes a number of systems for radiographic imaging using neutrons. Typical applications include the inspection of aircraft parts. This method is more advantageous, in many respects, than X-ray inspection due to the fact that neutrons are easily absorbed by hydride compounds of aluminum which exist in corroded areas. Also, neutron radiography is superior to its X-ray counterpart in the inspection of hydrogenous zones. This allows accurate inspection of continuity of pyrotechnic materials in their containers.

Prior art neutron radiographic imaging systems have suffered from image degradation due to a number of factors. A primary factor is the inherent existence of fast/epithermal neutrons originating at a neutron source which constitutes noise. Extraneous gamma and X-rays from the source also contribute noise. Room scattered thermalized neutrons also contribute a component to detected noise. Finally, detected ambient radiation reduces the available signal-to-noise ratio of a detected image.

In conventional systems, the source of neutrons is moderated by thermalizing the neutrons in a material such as polyethylene. However, since the source and detection of such prior art systems work in a DC mode, the noise factors outlined above continue through a measurement cycle.

In the past, several hardware approaches have been employed to ameliorate the situation. For instance, heavy shielding has been employed for fast neutrons and gamma rays around a moderator component of a system. Further, heavy shielding and 90° mirrors at the detector have been used. Clearly, this adds expense, complexity, and weight to a manufactured system.

The present invention is intended to increase the quality of a radiographic image by correspondingly increasing the signal-to-noise ratio of detection.

BRIEF DESCRIPTION OF THE PRESENT INVENTION

The present invention is intended to increase the quality of neutron radiographic images by decreasing the effects of noise previously indicated, particularly fast/epithermal neutrons and gamma rays. This is accomplished by gating a detector during an interval which is delayed in time from the pulse energization of a neutron source.

This pulsed source-gated detector approach significantly increases the quality of radiographic images by virtue of an increased signal-to-noise ratio. Further, the need for special shielding no longer exists so that the previously discussed hardware problems may be avoided.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1:
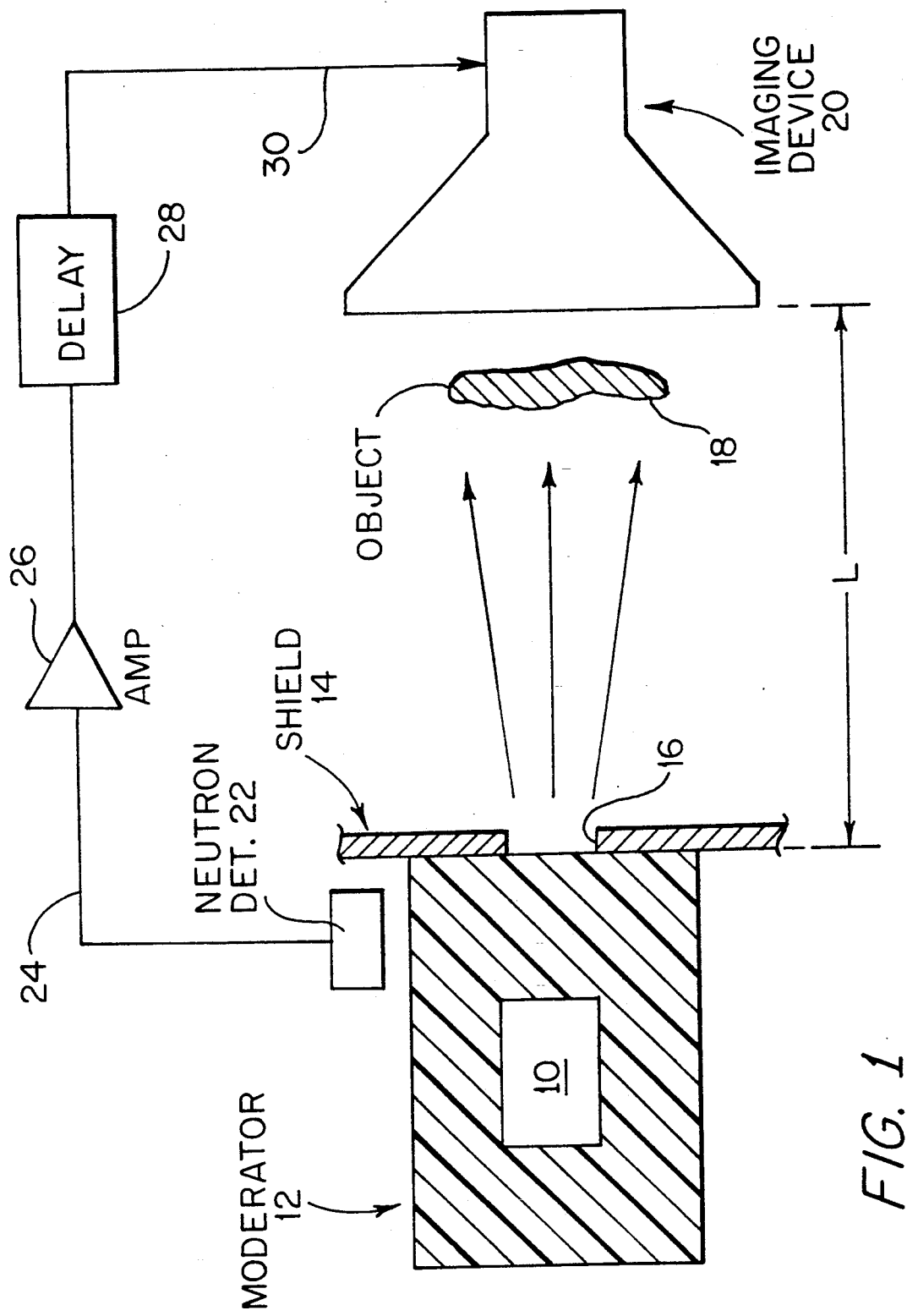
FIG. 1 is a schematic illustration of the present invention.

FIG. 1 illustrates a schematic view of the present invention incorporating a pulsed neutron source 10. Such sources, per se, are known in the prior art but it is to be stressed that the utilization in a system such as presented herein is believed to be patentable. The source may include a pulse accelerator, plasma focus source, or chopped reactor beam. The source is embedded within a moderator 12 for producing thermal neutrons. The moderator may be fabricated from an appropriate material such as pure polyethylene. The moderator is enclosed within a thermal neutron shield 14 having a slot 16 therein which collimates a pulsed thermal neutron beam. The shield may be fabricated from a neutron-absorbing material such as Cd, B, etc. An object 18 undergoing test is located in alignment with the slot 16 and is, in effect, positioned between the slot and the impinging surface of an imaging device 20. Such a device is conventional in nature and may be an image intensifier, CCD readout, etc. An appropriate imaging device is available from the Precise Optics Corp. of Bayshore, Long Island, N.Y.

Thus far, the novel aspect of the present invention is the incorporation of a pulsating source 10 in combination with a thermal neutron radiographic image detector. However, in order for the present system to operate properly, the imaging device 20 must be gated after an initial time delay. This will allow the passage of more quickly moving noise radiation across the face of the imaging device-without detection.

Figure 2:
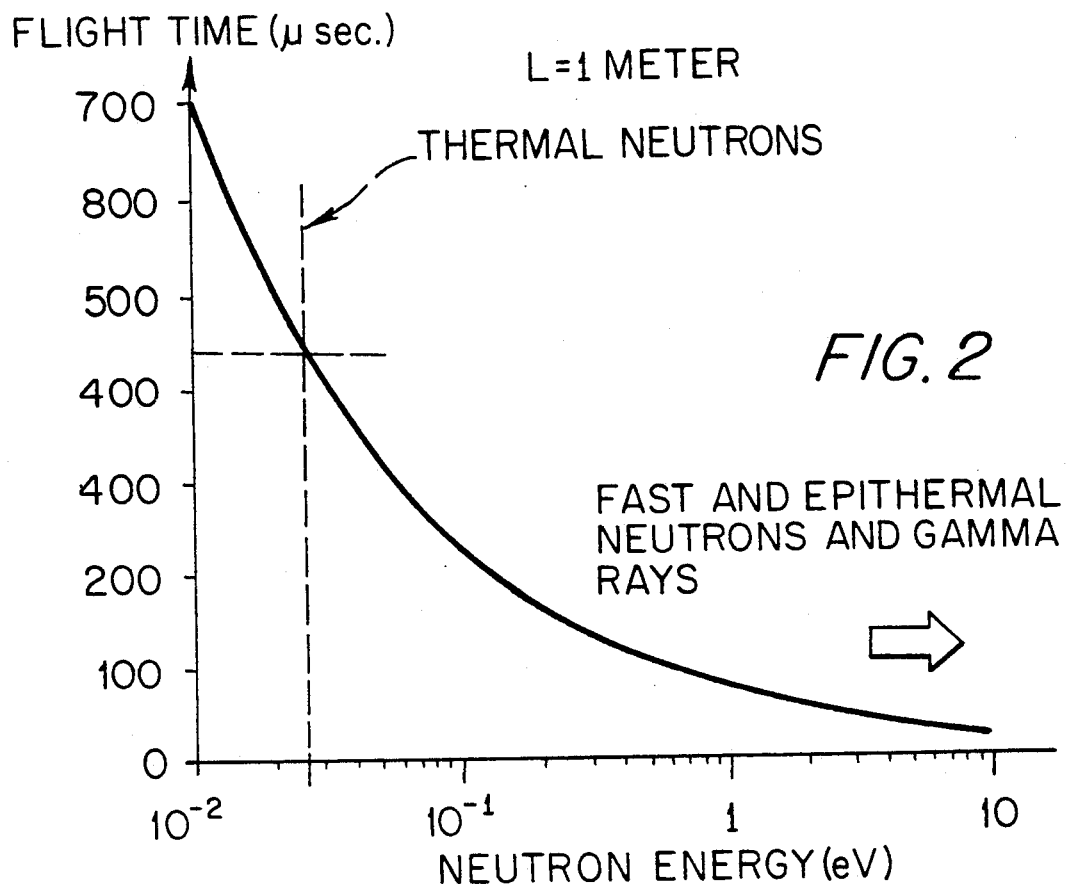
FIG. 2 is a plot of time of flight for low energy neutrons.

FIG. 2 illustrates the time of flight for low energy thermal neutrons as opposed to the unwanted sources of radiation, including fast and epithermal neutrons, as well as gamma rays.

Figure 3:
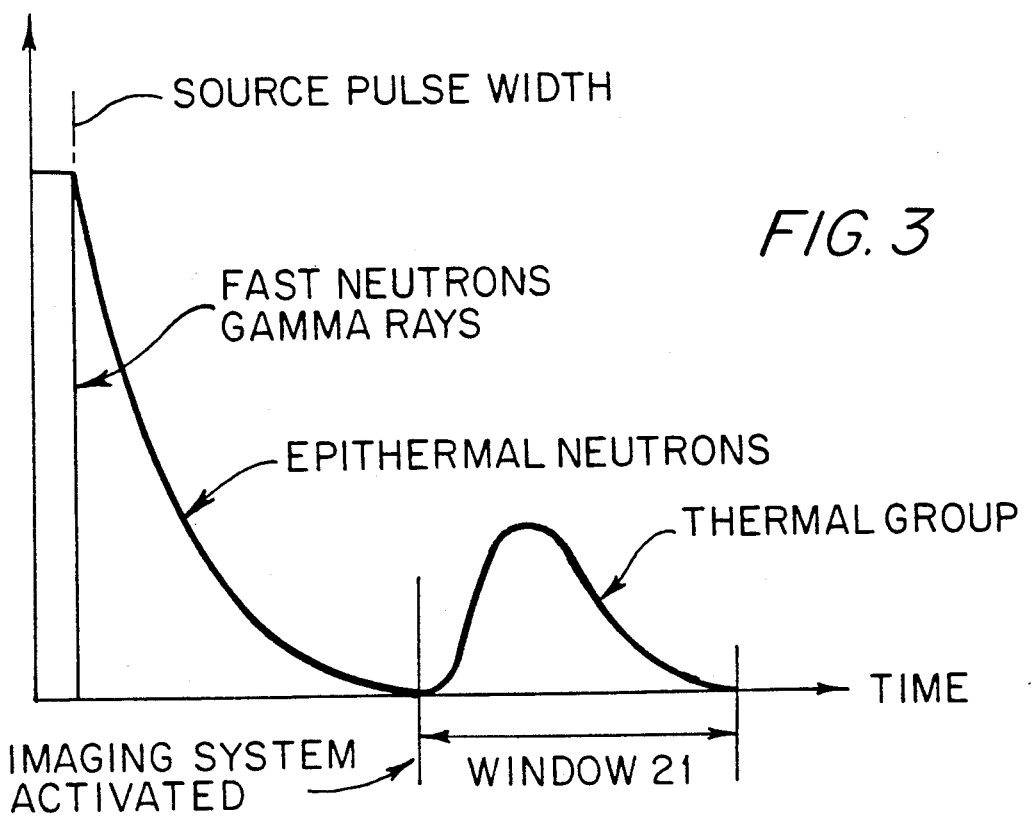
FIG. 3 is a plot of time of flight spectrum for pulsed neutron radiographic systems.

FIG. 3 indicates the spectrum of various extraneous radiation as well as the desirable thermal neutron group, all of which become generated when a neutron source is pulsed. As indicated, if the imaging device 20 of the system can be gated during the window period 21, the other, faster moving sources of noise radiation will pass and remain undetected.

To achieve this goal, a conventional neutron detector 22 is positioned within the shield 14 so that pulsed neutrons generated by the source may be detected. The output of the detector is connected to a signal amplifier 26 along line 24. The output of the amplifier undergoes a fixed time delay at 28 so that the imaging device 20 receives a delayed gating signal from the output of delay 28, along line 30. The delay is chosen to correspond with the time that thermal neutrons pass through the image and impinge upon imaging device 20. Since the neutron detector 22 detects the pulse interval from the source, the gating interval for image detection will be approximately the same. As a result, the signal-to-noise ratio of the detected signal during the window interval will be maximized. The result will be a higher quality image than is presently possible with DC systems.

It should be understood that the invention is not limited to the exact details of construction shown and described herein for obvious modifications will occur to persons skilled in the art.

I claim:

1. A method for radiographically inspecting an object comprising the steps:
   generating a source of pulsed neutrons;
   moderating the speed of the pulsed neutrons;
   collimating neutron flow along an axis intersecting the object;
   detecting the occurrence of pulsed neutrons and generating an electrical pulse signal therefrom;
   delaying the pulse signal by an interval sufficient to allow passage of non-moderated neutrons past a detection point located beyond the object; and
   gating an imaging device with the delayed pulse signal when moderated neutrons passing through the object arrive at the imaging device, the device being located at the detection point.

2. A gated neutron radiographic system for inspecting an object comprising:
   means for pulsing a source of neutrons;
   means for moderating the speed of neutrons generated by the source;
   means for collimating neutrons flowing along an axis intersecting the object;
   means for detecting the occurrence of pulsed neutrons and generating an electrical pulse signal therefrom;
   means connected to the detecting means for delaying the pulse signal by an interval sufficient to allow passage of non-moderated neutrons past a detection point located beyond the object; and
   means connecting the input of an imaging device with the delayed pulse signal, the device being located at the detection point, the delayed pulse gating the imaging device during an interval when moderated neutrons passing through the object have arrived at the imaging device.

3. A gated neutron radiographic system for inspecting an object comprising:
   means for pulsing a source of neutrons;
   means for moderating the speed of neutrons generated by the source;
   a neutron shield enclosing the moderating means and having an aperture therein for collimating neutrons flowing through the shield, along an axis intersecting the object;
   means for detecting the occurrence of the pulsed neutrons and generating an electrical pulse signal therefrom;
   means connected to the detecting means for delaying the pulse signal by an interval sufficient to allow passage of non-moderated neutrons past a detection point located beyond the object; and
   means connecting the input of an imaging device with the delayed pulse signal, the device being located at the detection point, the delayed pulse gating the imaging device during an interval when moderated neutrons passing through the object have arrived at the imaging device.

4. A gated neutron radiographic system for inspecting an object comprising:
   means for pulsing a source of neutrons;
   a block of polyethylene material surrounding the source for moderating the speed of neutrons generated by the source;
   a neutron shield enclosing the moderating means and having an aperture therein for collimating neutrons flowing through the shield, along an axis intersecting the object;
   means for detecting the occurrence of the pulsed neutrons and generating an electrical pulse signal therefrom;
   means connected to the detecting means for delaying the pulse signal by an interval sufficient to allow passage of non-moderated neutrons past a detection point located beyond the object;
   means connected between the pulsed neutron detecting means and the delaying means for amplifying the pulse signal; and
   means connecting the input of an imaging device with the delayed pulse signal, the device being located at the detection point, the delayed pulse signal gating the imaging device during an interval when moderated neutrons passing through the object have arrived at the imaging device.

* * * * *